US011607659B2

(12) United States Patent
Hatta

(10) Patent No.: US 11,607,659 B2
(45) Date of Patent: Mar. 21, 2023

(54) HOLLOW PARTICLES AND MANUFACTURING METHOD THEREOF, PORE FORMING MATERIAL, PARTICLES FOR COSMETICS, AND WEIGHT REDUCING MATERIAL

(71) Applicant: FUJIFILM Corporation, Tokyo (JP)

(72) Inventor: Masahiro Hatta, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/022,129

(22) Filed: Sep. 16, 2020

(65) Prior Publication Data

US 2021/0001299 A1   Jan. 7, 2021

Related U.S. Application Data

(63) Continuation of application No. PCT/JP2019/011599, filed on Mar. 19, 2019.

(30) Foreign Application Priority Data

Mar. 23, 2018 (JP) .............................. JP2018-056909
Oct. 26, 2018 (JP) .............................. JP2018-202215

(51) Int. Cl.
| | | |
|---|---|---|
| B01J 13/16 | (2006.01) | |
| B01J 13/20 | (2006.01) | |
| C08G 18/08 | (2006.01) | |
| C08G 18/32 | (2006.01) | |
| C08G 18/48 | (2006.01) | |
| C08G 18/77 | (2006.01) | |
| A61K 8/02 | (2006.01) | |
| C08J 9/32 | (2006.01) | |

(52) U.S. Cl.
CPC ............. B01J 13/16 (2013.01); B01J 13/20 (2013.01); C08G 18/0866 (2013.01); C08G 18/3228 (2013.01); C08G 18/48 (2013.01); C08G 18/771 (2013.01); A61K 8/0279 (2013.01); C08J 9/32 (2013.01)

(58) Field of Classification Search
None
See application file for complete search history.

(56) References Cited

U.S. PATENT DOCUMENTS

| | | | |
|---|---|---|---|
| 7,319,114 B2 | 1/2008 | Ohmura et al. | |
| 9,982,106 B2 | 5/2018 | Matsuno et al. | |
| 2010/0317753 A1* | 12/2010 | Keefe | B29C 44/3461 |
| | | | 524/575 |
| 2015/0259493 A1* | 9/2015 | Nederkoorn | C08J 9/0061 |
| | | | 521/97 |
| 2020/0317882 A1* | 10/2020 | Prissok | C08J 9/18 |
| 2021/0237035 A1* | 8/2021 | Gomes | C05G 5/14 |

FOREIGN PATENT DOCUMENTS

| | | |
|---|---|---|
| CN | 1525982 | 9/2004 |
| CN | 101041746 | 9/2007 |
| CN | 102256695 | 11/2011 |
| CN | 105246931 | 1/2016 |
| JP | H049319 | 1/1992 |
| JP | 2001199835 | 7/2001 |
| JP | 2001241162 | 9/2001 |
| JP | 2004009319 | 1/2004 |
| JP | 2006326457 | 12/2006 |
| JP | 2008247630 | 10/2008 |
| JP | 2017048323 | 3/2017 |
| JP | 2019034283 | 3/2019 |

OTHER PUBLICATIONS

"Office Action of Japan Counterpart Application" with English translation thereof, dated Jun. 8, 2021, p. 1-p. 8.
"International Search Report (Form PCT/ISA/210) of PCT/JP2019/011599," dated Jun. 25, 2019, with English translation thereof, pp. 1-5.
"Written Opinion of the International Searching Authority (Form PCT/ISA/237) of PCT/JP2019/011599," dated Jun. 25, 2019, with English translation thereof, pp. 1-12.
Office Action of China Counterpart Application, with English translation thereof, dated Nov. 22, 2021, pp. 1-25.
Dong Gui-Lin et al.," Research on Preparation of Coated Poly-α-olefin Microencapsulation Based on Polyurethane", Journal of Materials Engineering, Issue 7, Jul. 2010, with English abstract, pp. 6-13.
Han-Sheng Huang," A New Method for Producing Cross-linked Hollow Polymer Particles", New Chemical Materials, Issue 2, Mar. 1992, pp. 34-38.
Hu Jianqing et al.," Research on synthesis of diammonium hydrogen phosphate /polyurethane flame-retardant microcapsules by interfacial polymerization and its characterization", New Building Materials, vol. 36, Issue 11, Nov. 2009, with English abstract, pp. 24-28.
Office Action of China Counterpart Application, with English translation thereof, dated Mar. 17, 2022, pp. 1-21.
Office Action of China Counterpart Application, with English translation thereof, dated Jul. 28, 2022, pp. 1-21.
"Decision of Refusal of China Counterpart Application", dated Jan. 20, 2023, with partial English translation thereof, p. 1-p. 15.

\* cited by examiner

*Primary Examiner* — Jeffrey D Washville
(74) *Attorney, Agent, or Firm* — JCIPRNET

(57) ABSTRACT

According to an embodiment of the present invention, provided are hollow particles which have a wall portion containing polyurethane or polyurea, have an internal porous structure, and have a plurality of opening spaces blocked by the wall portion in an outermost portion of the porous structure, and a manufacturing method thereof, and a pore forming material, particles for cosmetics, and a weight reducing material.

15 Claims, No Drawings

HOLLOW PARTICLES AND MANUFACTURING METHOD THEREOF, PORE FORMING MATERIAL, PARTICLES FOR COSMETICS, AND WEIGHT REDUCING MATERIAL

CROSS-REFERENCE TO RELATED APPLICATIONS

This application is a continuation application of International Application No. PCT/JP2019/011599, filed Mar. 19, 2019, the disclosure of which is incorporated herein by reference in its entirety. Further, this application claims priority from Japanese Patent Application No. 2018-056909, filed Mar. 23, 2018, and Japanese Patent Application No. 2018-202215, filed Oct. 26, 2018, the disclosures of which are incorporated herein by reference in their entirety.

BACKGROUND OF THE INVENTION

1. Field of the Invention

The present disclosure relates to hollow particles and a manufacturing method thereof, and a pore forming material, particles for cosmetics, and a weight reducing material.

2. Description of the Related Art

Hollow particles having an internal space have been used in various fields.

Hollow particles are particles in which a gas is trapped in an outer shell formed of a resin. Accordingly, the hollow particles have a property of hardly transmitting heat or vibration, and are used in heat insulating materials, soundproofing materials, or the like, or used for filling a desired raw material to, for example, reduce the weight of a molded product.

In a case where hollow particles are used for such purposes, for example, the hollow particles are mixed, kneaded, or dispersed in a desired material to prepare a coating liquid or a molding material, and coating or molding is performed to manufacture a material containing the hollow particles or a material including a space formed by removing the hollow particles by heating.

Thermally expandable capsules have been widely used as an example of the hollow particles.

In addition, a melamine formaldehyde resin, an acrylic resin, and an inorganic material such as silica are frequently used as a material for forming a wall portion of the hollow particles.

As a specific example, a technique for forming hollow microcapsules by vaporizing a volatile solvent such as toluene contained in the microcapsules during or after formation of the microcapsules is disclosed (for example, see JP2006-326457A).

SUMMARY OF THE INVENTION

However, since hollow particles which have been used usually maintain a particle shape due to an outer shell formed of a resin, the hollow particles may be subjected to external stress and be deformed or destroyed depending on the properties of a material adapted to contain the hollow particles, a method such as mixing to be employed, or the like. There is also a concern that in a case where a significant variation occurs in the shape of the hollow particles contained in the material, a variation may occur in the quality of a product to be manufactured, and desired performance (for example, heat insulation performance) may not be expected.

Hollow microcapsules described in JP2006-326457A are also easily deformed in a case of being subjected to external stress since these are hollow.

In addition, the hollow particles may not be mixed or kneaded well with a material adapted to contain the hollow particles depending on the material for forming a wall portion, such as a polymer such as a melamine formaldehyde resin or an acrylic resin, or an inorganic material such as silica. For example, in a case where polyurethane or polyurea contains hollow particles, it is difficult to ensure good dispersibility with hollow particles according to the related art.

Thermally expandable capsules which have been proposed, whose volume change by heat is relatively large, are suitable for preparing a hollow structure having a smaller diameter in a case where the volume change by heat can be reduced. In addition, it is thought that in a case where an internal space is formed by finally performing a heating treatment as in a case of a pore forming material, it is preferable that the pore forming material does not remain after the heating treatment.

The present disclosure has been contrived in view of the above problems.

An object to be achieved by an embodiment of the present invention is to provide hollow particles having excellent deformation resistance.

An object to be achieved by another embodiment of the present invention is to provide a hollow particle manufacturing method of manufacturing hollow particles having excellent deformation resistance.

An object to be achieved by yet another embodiment of the present invention is to provide a pore forming material capable of forming a desired space, particles for cosmetics, and a weight reducing material.

Specific configurations for achieving the objects include the following aspects.

<1> Hollow particles which have a wall portion containing polyurethane or polyurea, have an internal porous structure, and have a plurality of opening spaces blocked by the wall portion in an outermost portion of the porous structure.

<2> The hollow particles according to <1>, in which the particles have a void volume of 10% to 90%.

<3> The hollow particles according to <1> or <2>, in which the particles have a spherical particle shape.

<4> The hollow particles according to any one of <1> to <3>, in which the particles have a volume-based median diameter of 0.1 μm to 500 μm.

<5> A pore forming material comprising: the hollow particles according to any one of <1> to <4>.

<6> The pore forming material according to <5>, in which the material is used for manufacturing porous ceramics or a porous resin.

<7> Particles for cosmetics which have oil absorbability or water absorbability, comprising: the hollow particles according to any one of <1> to <4>.

<8> A weight reducing material comprising: the hollow particles according to any one of <1> to <4>.

<9> A hollow particle manufacturing method comprising: a step of dispersing an oil phase containing a polyfunctional isocyanate compound, a compound having a boiling point of 90° C. to 150° C., and at least one of a polyol or a polyamine in a water phase to prepare a dispersion liquid; a step of heat-treating the dispersion liquid to polymerize at least the polyfunctional isocyanate compound, thereby forming a wall portion, and obtaining particles encapsulating the compound having a boiling point of 90° C. to 150° C.; and a step of removing the compound having a boiling point of 90° C. to 150° C. from the particles by a heating treatment to form hollow particles having a porous structure.

<10> The hollow particle manufacturing method according to <9>, in which a glass transition temperature of a resin as a wall material for the wall portion of the particles is equal to or lower than the boiling point of the compound having a boiling point of 90° C. to 150° C.

<11> The hollow particle manufacturing method according to <9> or <10>, in which a C log P value of the compound having a boiling point of 90° C. to 150° C., which is a partition coefficient, is 1 to 4.

According to an embodiment of the present invention, hollow particles having excellent deformation resistance are provided.

According to another embodiment of the present invention, a hollow particle manufacturing method of manufacturing hollow particles having excellent deformation resistance is provided.

According to yet another embodiment of the present invention, a pore forming material capable of forming a desired space, particles for cosmetics, and a weight reducing material are provided.

DESCRIPTION OF THE PREFERRED EMBODIMENTS

Hereinafter, hollow particles and a manufacturing method thereof, and a pore forming material, particles for cosmetics, and a weight reducing material according to an embodiment of the present disclosure will be described in detail.

In this specification, a numerical range expressed using "to" means a range including numerical values before and after "to" as a lower limit and an upper limit. In numerical ranges described in a stepwise manner in the present disclosure, an upper limit or a lower limit described in a certain numerical range may be substituted with an upper limit or a lower limit of another numerical range described in a stepwise manner. Furthermore, in a numerical range described in the present disclosure, an upper limit or a lower limit described in a certain numerical range may be substituted with a value shown in an example.

In this specification, the term "wall portion" and the term "shell" refer to an outer shell which forms hollow particles, and in a case where the hollow particles are microcapsules, the terms refer to a capsule wall. The term "core portion" or the term "core" refers to a portion encapsulated by a wall portion (shell).

In this specification, a material for forming a wall portion (shell) is referred to as a "wall material" or a "shell material", and a component contained in the core is referred to as a "core material".

In the hollow particles according to the embodiment of the present disclosure, the term "encapsulation" refers to a state in which a target is covered and confined by a wall portion (shell) of the hollow particles.

<Hollow Particles>

Hollow particles according to the embodiment of the present disclosure have a wall portion containing polyurethane or polyurea, and have an internal porous structure. In addition, the hollow particles have a structure in which a plurality of opening spaces in an outermost portion of the porous structure are blocked by the wall portion. The hollow particles according to the embodiment of the present disclosure have a high strength and elasticity against external stress due to the porous internal structure, and have an advantage in that these are hardly deformed or destroyed in a case of being subjected to external stress. Since polyurethane or polyurea is contained, the hollow particles are stable even with a thin wall portion, have little toxicity to the environment, and suppress adverse effects on the human body.

Polyurethane or polyurea may have a structure derived from a polyfunctional isocyanate compound.

Since hollow particles which have been used usually maintain a particle shape due to an outer shell (wall portion) formed of a resin, the hollow particles are easily deformed in a case of being subjected to external stress, and may be destroyed in some cases. This problem is also raised in the hollow microcapsules described in JP2006-326457A, and there is a problem in that the microcapsules are easily deformed by external stress. For example, hollow particles formed using a material such as a polymer such as a melamine formaldehyde resin or an acrylic resin, or an inorganic material such as silica may have poor affinity for a material adapted to contain the hollow particles, and mixing or kneading may not be easily performed. Furthermore, in a case of hollow particles known as thermally expandable capsule particles, there is a tendency that the particle diameter cannot be easily reduced, and it is expected to expand the uses of the particles in a case where the particle diameter can be further reduced.

In view of the above circumstances, in the present disclosure, a porous structure is formed in an internal portion covered with a wall portion containing polyurethane or polyurea, whereby the hollow particles have a shape which is not easily changed depending on the properties of a material adapted to contain the hollow particles or the mixing method to be employed, and have excellent deformation resistance.

Here, the deformation resistance includes a property in which the particle shape is hardly changed or a property in which the particles themselves are hardly destroyed and crushed.

The hollow particles according to the embodiment of the present disclosure have a wall portion which forms an outer shell of the particle, and an internal portion thereof surrounded by the wall portion is divided into a plurality of portions, and has a porous structure having a space in the divided portions. In the hollow particles according to the embodiment of the present disclosure, the wall portion is formed of polyurethane or polyurea, and the partition wall which forms the internal porous structure is also formed of polyurethane or polyurea.

The hollow particles according to the embodiment of the present disclosure have a structure surrounded by the wall portion. Accordingly, in an outermost portion of the porous structure assumed to have no wall portion in the hollow particles, a plurality of opening spaces exist, and each opening space is blocked by the wall portion.

The void volume of the porous structure of the hollow particles varies according to the use or purpose, and is preferably as large as possible to secure a certain space. The void volume is preferably in a range of 10% to 90%. The void volume is more preferably 20% or greater, and even more preferably 30% or greater from the viewpoint of ensuring at least a certain space in a desired region or material using the hollow particles.

In addition, from the viewpoint of improving the deformation resistance of the hollow particles (that is, improving the strength), a porous structure having a large number of pores or a porous structure having a thick partition wall for making the internal structure porous is preferably used. In this case, the void volume is more preferably 85% or less.

The void volume is obtained by cutting the hollow particles, observing the cut surfaces of the hollow particles with a scanning electron microscope (SEM), and calculating a ratio of the area of the hollow portion to the total area of the cut surface of the hollow particle.

The shape of the hollow particles is not particularly limited, and can be appropriately selected according to the use or purpose. For example, the hollow particles may have any one of a spherical shape, a rod-like shape, a plate shape, or the like. Among these, a spherical shape is preferable, and a true spherical shape is more preferable as the particle shape.

The volume-based median diameter (D50) of the hollow particles is preferably 0.1 μm to 500 μm. The volume-based median diameter is more preferably 1 μm or greater from the viewpoint of void volume, and 200 μm or less from the viewpoint of visibility.

The volume-based median diameter of the hollow particles can be controlled by changing dispersion conditions or the like.

Here, the volume-based median diameter of the hollow particles means a diameter with which the total particle volume is equal between the larger diameter side and the smaller diameter side in a case where the entire hollow particles are divided into two with the particle diameter at which the cumulative volume is 50% as a threshold value.

In the present disclosure, the volume-based median diameter of the hollow particles is measured using Microtrac MT3300EXII (manufactured by Nikkiso Co., Ltd.).

Examples of the hollow particles include microcapsules having a wall portion (shell) and a core portion (core) encapsulated by the wall portion.

Next, the wall portion of the hollow particles and the partition wall which forms the porous structure will be described.

In the present disclosure, the wall portion and the partition wall contain polyurethane or polyurea.

—Polyurethane, Polyurea—

Polyurethane and polyurea contained in the wall portion (shell) will be described.

In the present disclosure, the polyurethane and the polyurea preferably have a structure derived from a polyfunctional isocyanate compound (hereinafter, may be referred to as "polyisocyanate"). The polyisocyanate includes aromatic polyisocyanate and aliphatic polyisocyanate, and the polyisocyanate may be either bifunctional polyisocyanate or tri- or higher-functional polyisocyanate.

In the present disclosure, the polyurethane and the polyurea are preferably polymers having a structure derived from aromatic polyisocyanate and a structure derived from aliphatic polyisocyanate, and more preferably polymers having a structure derived from aromatic polyisocyanate in view of easily forming an internal porous structure.

In the present disclosure, the polyurethane and the polyurea are preferably polymers having a structure derived from tri- or higher-functional polyisocyanate in view of easily forming an internal porous structure.

The hollow particles according to the embodiment of the present disclosure containing polyurethane or polyurea include hollow particles containing polyurethane polyurea. Among hollow particles containing polyurethane or polyurea, hollow particles having a wall portion containing polyurethane polyurea are preferable.

Examples of the aliphatic polyisocyanate include trimethylene diisocyanate, hexamethylene diisocyanate, propylene-1,2-diisocyanate, butylene-1,2-diisocyanate, cyclohexylene-1,2-diisocyanate, cyclohexylene-1,3-diisocyanate, cyclohexylene-1,4-diisocyanate, dicyclohexylmethane-4,4'-diisocyanate, 1,4-bis(isocyanatomethyl)cyclohexane, 1,3-bis(isocyanatomethyl)cyclohexane, isophorone diisocyanate, lysine diisocyanate, and hydrogenated xylylene diisocyanate.

Examples of the aromatic polyisocyanate include m-phenylene diisocyanate, p-phenylene diisocyanate, 2,6-tolylene diisocyanate, 2,4-tolylene diisocyanate, naphthalene-1,4-diisocyanate, diphenylmethane-4,4'-diisocyanate, 3,3'-dimethoxy-biphenyl diisocyanate, 3,3'-dimethyldiphenylmethane-4,4'-diisocyanate, xylylene-1,4-diisocyanate, xylylene-1,3-diisocyanate, 4-chloroxylylene-1,3-diisocyanate, 2-methylxylylene-1,3-diisocyanate, 4,4'-diphenylpropane diisocyanate, and 4,4'-diphenylhexafluoropropane diisocyanate.

In the above description, examples of the bifunctional aliphatic polyisocyanate and aromatic polyisocyanate include diisocyanate compounds, but trifunctional triisocyanate compounds and tetrafunctional triisocyanate compounds inferred from the diisocyanate compounds are also included.

Adducts of the polyisocyanate and bifunctional alcohols or phenols such as ethylene glycol-based compounds or bisphenol-based compounds are also included.

Examples of the condensates, polymers, or adducts using the polyisocyanate include biurets or isocyanurates, which are trimers of the bifunctional polyisocyanates, compounds polyfunctionalized as adducts of bifunctional polyisocyanate compounds and polyols such as trimethylol propane, formalin condensates of benzene isocyanate, polymers of polyisocyanate compounds having a polymerizable group such as methacryloyloxyethyl isocyanate, and lysine triisocyanate.

The polyisocyanate compound is described in "Polyurethane Resin Handbook" (edited by Keiji Iwata, published by NIKKAN KOGYO SHIMBUN, LTD. (1987)).

The shell of the hollow particles preferably contain a polymer of tri- or higher-functional polyisocyanate.

Examples of the tri- or higher-functional polyisocyanate include tri- or higher-functional aromatic polyisocyanate compounds and tri- or higher-functional aliphatic polyisocyanate compounds. As examples of the tri- or higher-functional polyisocyanate compound, polyisocyanate compounds (adduct type) tri- or higher-functionalized as adducts of compounds having three or more active hydrogen groups in the molecule (tri- or higher-functional, e.g., polyol, polyamine, or polythiol) and bifunctional polyisocyanate compounds (compounds having two polyisocyanate groups in the molecule), and trimers (biuret type or isocyanurate type) of bifunctional polyisocyanate compounds are also preferable.

Specific examples of the tri- or higher-functional polyisocyanate compound include an adduct of trimethylolpropane and 2,6-tolylene diisocyanate, 2,4-tolylene diisocyanate, or hexamethylene diisocyanate, a biuret, and an isocyanurate.

As the adduct type tri- or higher-functional polyisocyanate compound, a commercially available product may be used, and examples of the commercially available product include TAKENATE (registered trademark) D-102, D-103, D-103H, D-103M2, P49-75S, D-110N, D-120N (isocyanate value=3.5 mmol/g; tri- or higher-functional aromatic isocyanate compound), D-140N, and D-160N (all manufactured by Mitsui Chemicals, Inc.), DESMODUR (registered trademark) L75 and UL57SP (manufactured by Sumika Bayer Urethane Co., Ltd.), CORONATE (registered trademark) HL, HX, and L (manufactured by Nippon Polyurethane Industry Co., Ltd.), P301-75E (manufactured by Asahi Kasei Corporation), and BURNOCK (registered trademark) D-750 (manufactured by DIC Corporation; tri- or higher-functional aromatic isocyanate compound).

Among these, at least one selected from TAKENATE (registered trademark) D-110N, D-120N, D-140N, and D-160N manufactured by Mitsui Chemicals, Inc., and BURNOCK (registered trademark) D-750 manufactured by DIC Corporation is more preferable as the adduct type tri- or higher-functional polyisocyanate compound.

As the isocyanurate type tri- or higher-functional polyisocyanate compound, a commercially available product may be used, and examples thereof include TAKENATE (registered trademark) D-127N, D-170N, D-170HN, D-172N, D-177N, and D-204 (manufactured by Mitsui Chemicals, Inc.), SUMIDUR N3300, DESMODUR (registered trademark) N3600, N3900, and Z4470BA (Sumika Bayer Urethane Co., Ltd.), CORONATE (registered trademark) HX and HK (manufactured by Nippon Polyurethane Industry Co., Ltd.), and DURANATE (registered trademark) TPA-100, TKA-100, TSA-100, TSS-100, TLA-100, and TSE-100 (manufactured by Asahi Kasei Corporation).

As the biuret type tri- or higher-functional polyisocyanate compound, a commercially available product may be used, and examples thereof include TAKENATE (registered trademark) D-165N and NP1100 (manufactured by Mitsui Chemicals, Inc.), DESMODUR (registered trademark) N3200 (Sumika Bayer Urethane Co., Ltd.), and DURANATE (registered trademark) 24A-100 (manufactured by Asahi Kasei Corporation).

The thickness of the wall portion of the hollow particles (wall thickness) is preferably 0.01 μm to 10 μm. In a case where the wall thickness of the hollow particles is 0.01 μm or greater, the hollow particles are hardly deformed. In a case where the wall thickness of the hollow particles is 10 μm or less, the hollow particles have an advantage of having an increased void volume.

From the same viewpoint as above, the wall thickness of the hollow particles is more preferably 0.05 μm to 5 μm, even more preferably 0.1 μm to 2 μm, and particularly preferably 0.1 μm to 1 μm.

The wall thickness is an average obtained by averaging wall thicknesses (μm) of five hollow particles measured by a scanning electron microscope (SEM).

Specifically, a liquid containing hollow particles is applied to a support and dried to form a coating film. A cross-sectional slice of the obtained coating film is prepared. The cross-section is observed using an SEM, and 5 hollow particles are randomly selected. Wall thicknesses are measured by observing the cross-sections of the hollow particles, and an average thereof is calculated to obtain the wall thickness.

Regarding the hollow particles according to the embodiment of the present disclosure, the expression "high monodispersibility" means that the range of particle size distribution is narrow (that is, there is little variation in the particle diameter), and the expression "low monodispersibility" means that the range of particle size distribution is wide (that is, there are many variations in the particle diameter).

More specifically, the level of monodispersibility of the hollow particles can be expressed by using a CV value (coefficient of variation). Here, the CV value is a value obtained by the following formula.

CV value (%)=(standard deviation/volume average particle diameter)×100

The lower the CV value, the higher the monodispersibility of the hollow particles, and the higher the CV value, the lower the monodispersibility of the hollow particles.

In the present disclosure, the volume average particle diameter and the standard deviation are calculated using MICROTRAC MT3300EXII (manufactured by Nikkiso Co., Ltd.).

For example, the expression "high monodispersibility" of the hollow particles may also mean that the CV value of the particle size distribution of the hollow particles is preferably 40% or less, more preferably 35% or less, even more preferably 30% or less, and most preferably 25% or less. In a case where the CV value is in the above range, the monodispersibility of the particle diameter of the hollow particles is high, whereby handling of the hollow particles, controlling exhibition of functions, and the like are facilitated.

Examples of the form of the hollow particles include a hollow particle dispersion liquid containing hollow particles dispersed therein and a powder of hollow particles, and the hollow particles preferably have a powder form.

The core portion (core) of the hollow particles according to the embodiment of the present disclosure, encapsulated by the wall portion (shell) preferably exists as a space.

A core material may be encapsulated in the core portion according to the use and the like. Examples of the core material include solvents, auxiliary solvents, and additives.

(Solvent)

The core material may contain a solvent as an oil component.

Examples of the solvent include fatty acid ester-based compounds such as glyceryl tri(capryl-caprate) and isopropyl myristate, aromatic hydrocarbons such as alkylnaphthalene-based compounds such as diisopropyl naphthalene, diarylalkane-based compounds such as 1-phenyl-1-xylylethane, alkylbiphenyl-based compounds such as isopropyl biphenyl, triarylmethane-based compounds, alkylbenzene-based compounds, benzylnaphthalene-based compounds, diarylalkylene-based compounds, and arylindane-based compounds; aliphatic hydrocarbons such as dibutyl phthalate and isoparaffin; natural animal or vegetable oils such as camellia oil, soybean oil, corn oil, cottonseed oil, rapeseed oil, olive oil, coconut oil, castor oil, and fish oil; and high-boiling fractions of natural products such as mineral oil.

(Auxiliary Solvent)

As the core material, an auxiliary solvent may be optionally contained as an oil phase component for increasing the solubility of the wall material (shell material) which forms the wall portion of the hollow particles in the oil phase.

Examples of the auxiliary solvent include ketone-based compounds such as methyl ethyl ketone, ester-based compounds such as ethyl acetate, and alcohol-based compounds such as isopropyl alcohol. Preferably, the auxiliary solvent has a boiling point of 130° C. or lower. The auxiliary solvent does not include the above solvents.

(Additive)

For example, additives such as an ultraviolet absorber, a light stabilizer, an antioxidant, wax, and an odor suppressing agent can be optionally encapsulated in the microcapsules.

<Hollow Particle Manufacturing Method>

A hollow particle manufacturing method according to the embodiment of the present disclosure has a step of dispersing an oil phase containing a polyfunctional isocyanate compound, a compound having a boiling point of 90° C. to 150° C., and at least one of a polyol or a polyamine in a water phase to prepare a dispersion liquid (hereinafter, dispersion step), a step of heat-treating the dispersion liquid to polymerize at least the polyfunctional isocyanate compound, thereby forming a wall portion, and obtaining particles encapsulating the compound having a boiling point of 90° C. to 150° C. (hereinafter, particle forming step), and a step of removing the "compound having a boiling point of 90° C. to 150° C." from the particles by a heating treatment to form hollow particles having a porous structure (hereinafter, hollow particle forming step).

—Dispersion Step—

In the dispersion step, an oil phase containing a polyfunctional isocyanate compound, a compound having a boiling point of 90° C. to 150° C., and at least one of a polyol or a polyamine is dispersed in a water phase to prepare a dispersion liquid.

An emulsion emulsified using a surfactant may be prepared as the dispersion liquid. In the preparation of an emulsion, the emulsion can be prepared by dispersing an oil phase containing a solvent and a shell material in a water phase containing an emulsifier.

(Oil Phase)

In the present disclosure, the oil phase contains at least a polyfunctional isocyanate compound as a shell material, a compound having a boiling point of 90° C. to 150° C. as an organic solvent, and at least one of a polyol or a polyamine, and may optionally contain other components such as an auxiliary solvent and additives.

Details of the polyfunctional isocyanate compound, the auxiliary solvent, and the additive are the same as those of the core component of the microcapsules described above, and detailed description thereof will be omitted here.

—Compound Having Boiling Point of 90° C. to 150° C.—

The oil phase contains at least one kind of compound having a boiling point of 90° C. to 150° C.

In a case where the compound in the core component has a boiling point in a range of 90° C. to 150° C., as will be described later, in the process in which the dispersion liquid containing particles dispersed therein, which are a precursor of the hollow particles, is heat-treated to obtain particles encapsulating the "compound having a boiling point of 90° C. to 150° C., and then a heating treatment is further performed to obtain the hollow particles, the compound may be removed, and the hollow particles may have an internal porous structure.

The boiling point of the compound having a boiling point of 90° C. to 150° C. is preferably equal to or higher than a glass transition temperature (Tg; ° C.) of a resin (preferably polyurethane or polyurea) as a wall material for the wall portion of the particles formed in the particle forming step to be described later from the viewpoint of easily forming the porous structure.

From this point of view, the boiling point is preferably 100° C. to 140° C.

The boiling point means a boiling point under 1 atm (101,325 Pa).

The boiling point can be determined by an ordinary method, for example, an atmospheric pressure distillation test method defined in item 4 of JIS K2254: 1998. The boiling point can also be measured using a boiling point meter. As the boiling point meter, BPM-2000 (manufactured by DKK-TOA CORPORATION, atmospheric pressure distillation test method), DosaTherm 300 (manufactured by Dosatec GmbH), or the like can be used.

The compound having a boiling point of 90° C. to 150° C. preferably has a C log P value of 1 to 4, which is a partition coefficient, more preferably 1.5 to 3, and even more preferably 1.5 to 2.

The smaller the C Log P value, the higher the polarity of the compound.

Accordingly, in the present disclosure, in a case where the C log P value of the "compound having a boiling point of 90° C. to 150° C." contained in the oil phase is 1 to 4, the polyfunctional isocyanate compound existing in the same phase is hard to move to the oil-water interface in a case where the dispersed particles are prepared, and the reaction of the polyfunctional isocyanate compound easily proceeds in the oil phase. As a result, a porous structure is more easily formed inside the particles obtained by forming the wall portion.

The C Log P value is calculated using ChemBioDraw Ultra 13.0.

Examples of the compound having a boiling point of 90° C. to 150° C. include organic solvents and fragrances.

Examples of the organic solvents include 1,1,2,2-tetrachloroethane (boiling point: 146° C., C log P=2.64), p-xylene (boiling point: 138° C., C log P=3.14), chlorobenzene (boiling point: 132° C., C log P=2.86), isobutyl acetate (boiling point: 118° C., C log P=1.64), butyl acetate (boiling point: 126° C., C log P=1.77), propyl acetate (boiling point: 97° C., C log P=1.24), styrene (boiling point: 145° C., C log P=2.89), tetrachloroethylene (boiling point: 121° C., C log P=3.48), and toluene (boiling point: 111° C., C log P=2.64).

Examples of the fragrances include isoamyl acetate (boiling point: 142° C., C log P=2.17), ethyl propionate (boiling point: 99° C., C log P=1.24), ethyl butyrate (boiling point: 121° C., C log P=1.77), γ-nonalactone (boiling point: 136° C., C log P=1.83), and amyl acetate (boiling point: 149° C., C log P=1.62).

The content of the compound having a boiling point of 90° C. to 150° C. in the oil phase may be in a range of 10 mass % to 95 mass % with respect to the total mass of the oil phase, and from the viewpoint of increasing the void volume, the higher the content is preferably as high as possible. The content of the compound having a boiling point of 90° C. to 150° C. is more preferably 30 mass % to 90 mass %, and even more preferably 50 mass % to 90 mass % with respect to the total mass of the oil phase from the viewpoint of a balance between the void volume and the deformation resistance of the hollow particles.

—Polyfunctional Isocyanate Compound—

Details of the polyfunctional isocyanate compound as a shell material are as described in the section of the microcapsules described above, and detailed description thereof will be omitted here.

The content of the polyfunctional isocyanate compound in the oil phase can be appropriately adjusted according to the size, void volume, wall portion thickness, and the like of the hollow particles.

Specifically, the content of the polyfunctional isocyanate compound in the oil phase may be in a range of 1 mass % to 90 mass % with respect to the total mass of the oil phase. The content of the polyfunctional isocyanate compound is preferably 5 mass % to 70 mass %, more preferably 25 mass % to 65 mass %, and even more preferably 25 mass % to 50 mass % from the viewpoint of increasing the void volume.

—Polyol, Polyamine—

The oil phase contains at least one of a polyol or a polyamine.

A polyol is a molecule having an optional structure having two or more hydroxyl groups per molecule. The polyol preferably has three or more hydroxyl groups, and may have, for example, 4 or 8 hydroxyl groups per molecule.

The polyol may be either a synthetic polyol or a natural polyol, and may be a molecule having a linear, branched, or cyclic structure.

Examples of the polyol include ethylene glycol, polyethylene glycol (the degree of polymerization may be 2, 3, 4, 5, 6 or greater), propylene glycol, polypropylene glycol (the degree of polymerization is 2, 3, 4, 5, 6 or greater), neopentyl glycol, 3-methyl-1,3-butanediol, 1,3-butylene glycol, isoprene glycol, 1,2-pentanediol, 1,2-hexanediol, glycerin, polyglycerin (the degree of polymerization may be 2, 3, 4, 5, 6 or greater), pentaerythritol, and N,N,N',N'-tetrakis(2-hydroxypropyl)ethylenediamine.

As the polyol, a commercially available product may be used, and examples of the commercially available product include ADEKA POLYETHER (P series, BPX series, G series, T series, EDP series, SC series, SP series, AM series, BM series, CM series, PR series, GR series, FC-450, NS-2400, YT-101, F7-67, #50, F1212-29, YG-108, V14-90, Y65-55, and the like) manufactured by ADEKA CORPORATION.

A polyamine includes diamine, triamine, tetraamine, and the like, and examples thereof include triethanolamine, hexamethylenediamine, and tetraethylenepentamine.

As the polyamine, a commercially available product may be used, and examples of the commercially available product include ethylene amine (examples: ethylenediamine, diethylenetriamine, triethylenetetramine, tetraethylenepentamine, pentaethylenehexamine, aminoethylpiperazine, piperazine, polyate, and the like) manufactured by Tosoh Corporation.

From the viewpoint of increasing the void volume, the total content of the polyol and the polyamine in the oil phase is preferably in a range of 0.1 mass % to 20 mass %, more preferably in a range of 0.1 mass % to 10 mass %, and even more preferably in a range of 0.1 mass % to 5 mass % with respect to the total mass of the oil phase.

Particles encapsulating the "compound having a boiling point of 90° C. to 150° C.", which are a precursor of the hollow particles, are obtained by forming a wall portion in the particle forming step to be described later. From the viewpoint of making it easy to make the inside of the particles hollow in a case where a heating treatment is further performed in the subsequent hollow particle forming step, the resin as a wall material for the wall portion of the particles preferably has a glass transition temperature (Tg; ° C.) not higher than the boiling point of the "compound having a boiling point of 90° C. to 150° C.".

The glass transition temperature (Tg) of the resin of the wall portion is preferably 10° C. or higher lower than the boiling point of the "compound having a boiling point of 90° C. to 150° C." for the same reason as above.

The glass transition temperature (Tg) of the resin of the wall portion is a value measured using a differential scanning calorimeter (DSC).

(Water Phase)

In the present disclosure, the water phase preferably contains at least an aqueous solvent and an emulsifier.

—Aqueous Medium—

Examples of the aqueous medium of the present disclosure include water, and water and alcohol, and ion exchange water or the like can be used.

The content of the aqueous medium in the water phase is preferably 20 mass % to 80 mass %, more preferably 30 mass % to 70 mass %, and even more preferably 40 mass % to 60 mass % with respect to the total mass of the emulsion obtained by emulsifying and dispersing the oil phase in the water phase.

—Emulsifier—

The emulsifier contains a dispersant, a surfactant, or a combination thereof.

Examples of the dispersant include polyvinyl alcohol and modified products thereof (for example, anion-modified polyvinyl alcohol), polyacrylic acid amide and derivatives thereof, ethylene-vinyl acetate copolymers, styrene-maleic anhydride copolymers, ethylene-maleic anhydride copolymers, isobutylene-maleic anhydride copolymers, polyvinylpyrrollidone, ethylene-acrylic acid copolymers, vinyl acetate-acrylic acid copolymers, carboxymethyl cellulose, methyl cellulose, casein, gelatin, starch derivatives, gum arabic, and sodium alginate, and polyvinyl alcohol is preferable.

As the dispersant, a commercially available product may be used, and for example, KURARAY POVAL (registered trademark) series manufactured by KURARAY CO., LTD. (examples: 3-98, 5-98, 28-98, 60-98, 27-96, 3-88, 5-88, 22-88, 44-88, 95-88, 48-80, L-10, 25-88KL, 32-97KL, 3-86SD, LM-20, LM-10HD, 105-88KX, 200-88KX, and the like), granules J series manufactured by Japan Vam & Poval Co., Ltd. (JC-25, JC-33, JC-40, JF-02, JF-03, JF-04, JF-05, JF-10, JF-17, JF-17L, JF-20, JM-17, JM-17L, JM-23, JM-26, JM-33, JT-05, JT-13Y, JP-03, JP-04, JP-05, JP-10, JP-15, JP-18, JP-20, JP-24, JP-33, JP-45, JP-24E, JL-05E, JL-18E, JL-22E, JL-25E, JR-05, JF-17S, JP-05S, JP-18S, JP-20S, JP-24S, and the like), V series (V, VC-10, VC-13, VC-20, VF-17, VF-20, VM-17, VT-13KY, VP-18, VP-20, and the like), GOHSENOL manufactured by Nippon Synthetic Chemical Industry Co., Ltd. (N-300, NL-05, A-300, AL-06R, GH-23, GH-22, GH-20, GH-20R, GH-17R, GM-14R, GM-14L, GL-05, GL-03, KH-20, KH-17, KL-05, KL-03, KP-08R, NK-05R, and the like), GOHSENEX (Z-100, Z-200, Z-205, Z-210, Z-220, Z-300, Z-320, Z-410, K-434, L-3266, CKS-50, T-330H, T-330, T-350, LW-100, LW-200, EG-05, EG-40, WO-320N, and the like), and DENKA POVAL manufactured by Denka Corporation (K-05, K-17E, K-17C, H-12, H-17, H-24, B-05, B-17, B-20, B-24, B-33, K-177, NP-05F, EP-130, U-12, PC-1000, PC-2000, PC-5000F, PC-5500, W-100, D-100, F-3005, B-24N, W-20N, W-24N, MP-10, MP-10R, and the like) can be used.

Preferably, the dispersant does not react or very hardly reacts with the shell material. For example, a dispersant such as gelatin, having a reactive amino group in its molecular chain, is previously treated to lose its reactivity.

Examples of the surfactant include nonionic surfactants, anionic surfactants, cationic surfactants, and amphoteric surfactants. The surfactants may be used alone or in combination of two or more kinds thereof.

The nonionic surfactant is not particularly limited, and surfactants which have been known can be used.

Examples of the nonionic surfactant include polyoxyethylene alkyl ether-based compounds, polyoxyethylene alkylphenyl ether-based compounds, polyoxyethylene polystyryl phenyl ether-based compounds, polyoxyethylene polyoxypropylene alkyl ether-based compounds, glycerin fatty acid partial ester-based compounds, sorbitan fatty acid partial ester-based compounds, pentaerythritol fatty acid partial ester-based compounds, propylene glycol monofatty acid ester-based compounds, sucrose fatty acid partial ester-based compounds, polyoxyethylene sorbitan fatty acid partial ester-based compounds, polyoxyethylene sorbitol fatty acid partial ester-based compounds, polyethylene glycol fatty acid ester-based compounds, polyglycerin fatty acid partial ester-based compounds, polyoxyethylenated castor oil-based compounds, polyoxyethylene glycerin fatty acid partial ester-based compounds, fatty acid diethanolamide-based compounds, N,N-bis-2-hydroxyalkyl amine-based compounds, polyoxyethylene alkylamine, triethanolamine fatty acid ester, trialkylamine oxide, polyethylene glycol, and copolymers of polyethylene glycol and polypropylene glycol.

The anionic surfactant is not particularly limited, and surfactants which have been known can be used.

Examples of the anionic surfactant include fatty acid salt, abietic acid salt, hydroxyalkane sulfonic acid salt, alkane sulfonic acid salt, dialkylsulfosuccinate ester salt, linear alkylbenzene sulfonic acid salt, branched alkylbenzene sulfonic acid salt, alkylnaphthalene sulfonic acid salt, alkylphenoxy polyoxyethylene propyl sulfonic acid salt, polyoxyethylene alkyl sulfophenyl ether salt, N-methyl-N-oleyl taurine sodium salt, N-alkyl sulfosuccinic acid mono-amido disodium salt, petroleum sulfonic acid salt, sulfated beef tallow oil, sulfuric acid ester salt of fatty acid alkyl ester, polyoxyethylene alkyl ether sulfuric acid ester salt, fatty acid monoglyceride sulfuric acid ester salt, polyoxyethylene alkyl phenyl ether sulfuric acid ester salt, polyoxyethylene styryl phenyl ether sulfuric acid ester salt, alkyl phosphoric acid ester salt, polyoxyethylene alkyl ether phosphoric acid ester salt, polyoxyethylene alkylphenyl ether phosphoric acid ester salt, a partially saponified product of a styrene-maleic anhydride copolymer, a partially saponified product of an olefin-maleic anhydride copolymer, naphthalene sulfonic acid salt formalin condensate, salt of alkyl polyoxyalkylene sulfoalkyl ether, and salt of alkenyl polyoxyalkylene sulfoalkyl ether.

The cationic surfactant is not particularly limited, and surfactants which have been known can be used.

Examples of the cationic surfactant include alkylamine salt, quaternary ammonium salt (for example, hexadecyltrimethylammonium chloride), polyoxyethylene alkylamine salt, and a polyethylene polyamine derivative.

The amphoteric surfactant is not particularly limited, and surfactants which have been known can be used.

Examples of the amphoteric surfactant include carboxybetaine, aminocarboxylic acid, sulfobetaine, amino sulfuric acid ester, and imidazoline.

The concentration of the emulsifier is preferably greater than 0 mass % and 20 mass % or less, more preferably 0.005 mass % to 10 mass %, even more preferably 0.01 mass % to 10 mass %, and still more preferably 1 mass % to 5 mass % with respect to the total mass of the emulsion.

The water phase may optionally contain other components such as an ultraviolet absorber, an antioxidant, and a preservative. In a case where other components are contained, the content thereof is preferably greater than 0 mass % and 20 mass % or less, more preferably greater than 0.1 mass % and 15 mass % or less, and even more preferably greater than 1 mass % and 10 mass % or less with respect to the total mass of the water phase.

(Dispersion)

Dispersion means dispersing the oil phase as oil droplets in the water phase in the present disclosure, and includes emulsifying with the water phase containing a surfactant (emulsifier).

Dispersion can be performed using a unit which is usually used for dispersing an oil phase and a water phase, such as a homogenizer, a Manton-Gaulin, an ultrasonic disperser, a dissolver, a Keddy mill, or other known dispersion apparatuses.

The mixing ratio of the oil phase to the water phase (oil phase/water phase; based on mass) is preferably 0.1 to 1.5, more preferably 0.2 to 1.2, and even more preferably 0.4 to 1.0. In a case where the mixing ratio is in the range of 0.1 to 1.5, it is possible to maintain an appropriate viscosity, and excellent manufacturing suitability and emulsion stability are obtained.

—Particle Forming Step—

In the particle forming step, the dispersion liquid obtained in the dispersion step is heat-treated to polymerize at least the polyfunctional isocyanate compound, thereby forming a wall portion, and obtaining particles encapsulating the "compound having a boiling point of 90° C. to 150° C.".

Due to the heating treatment, the polyfunctional isocyanate compound is polymerized at the oil-water interface in the dispersion liquid, and thus a wall portion is formed, and the "compound having a boiling point of 90° C. to 150° C." is encapsulated as a core component.

In this step, at least the polyfunctional isocyanate compound is polymerized. Polymerization is performed by polymerizing the shell material contained in the oil phase in the dispersion liquid at the interface with the water phase. Thus, a wall portion (shell) is formed. In this case, a dispersion liquid (for example, an aqueous dispersion of microcapsules) in which particles encapsulating the oil phase are dispersed in the water phase is prepared.

In the formation of the wall portion, the dispersion liquid is heat-treated. The temperature for the heating treatment is usually preferably 40° C. to 100° C., and more preferably 50° C. to 80° C.

In addition, the heating time depends on the heating temperature, and is usually preferably about 0.5 to 10 hours, and more preferably about 1 to 5 hours. The higher the heating temperature, the shorter the polymerization time. However, from the viewpoint of facilitating the formation of a porous structure inside the particles, it is desirable to perform the polymerization at a low temperature for a long period of time.

In order to prevent the particles from aggregating during the polymerization, an aqueous solution (for example, water, acetic acid aqueous solution, or the like) is preferably further added to reduce the probability of collision between the particles, and stirring is also preferably sufficiently performed.

A dispersant for preventing aggregation may be further added during the polymerization.

A charge control agent such as nigrosine or other optional auxiliary agents can be further added. The auxiliary agent can be added at the time of forming the wall portion or at an optional time point.

—Hollow Particle Forming Step—

In the hollow particle forming step, a heating treatment is further performed to remove the "compound having a boiling point of 90° C. to 150° C." from the particles formed in the particle forming step. Accordingly, hollow particles having a porous structure are obtained.

In this step, a heating treatment is performed on the dispersion liquid (for example, an aqueous dispersion of microcapsules) prepared in the particle forming step. In this case, the particles are preferably heat-treated after the aqueous medium in the dispersion liquid is previously removed.

Specifically, it is preferable that powderization is performed by separating the aqueous medium from the particles through a drying treatment performed on the dispersion liquid, and the obtained powder is heat-treated. Accordingly, the particles encapsulating the core component taken out from the dispersion liquid (that is, precursor particles of hollow particles) are heated, and the "compound having a boiling point of 90° C. to 150° C." encapsulated in the particles is efficiently released to the outside through the wall portion of the particles. Accordingly, it is possible to form hollow particles.

The heating temperature during the heating treatment in this step is preferably equal to or higher than the boiling point of the encapsulated "compound having a boiling point of 90° C. to 150° C.", and more preferably 150° C. or higher from the viewpoint of efficiently removing the "compound having a boiling point of 90° C. to 150° C.". The upper limit of the heating temperature is not particularly limited, and may be, for example, 200° C. or lower.

The heating time during the heating treatment depends on the heating temperature and the amount of particles. Accordingly, the heating time may be appropriately selected according to the conditions such as the heating temperature during the heating. For example, in the above heating temperature range, the heating time can be set to 1 hour to 5 hours, or may be 1 hour to 3 hours.

In this step, the heating treatment can be performed using a known heater, and for example, a hot air blower (dryer), an oven, an infrared heater, or the like can be used.

In a case where the aqueous medium in the dispersion liquid is previously removed before the heating treatment for the particles, the aqueous medium may be removed using a known drying device. For example, a spray dryer is preferably used. Dehydration using a filtration device may be performed.

<Pore Forming Material>

A pore forming material according to the embodiment of the present disclosure includes the hollow particles according to the embodiment of the present disclosure described above.

The hollow particles according to the embodiment of the present disclosure have deformation resistance due to the internal porous structure thereof. Accordingly, in a case where the pore forming material is mixed into a desired material, the hollow particles are hardly deformed due to the properties of the material, the mixing method, or the like. Therefore, it is easy to reproduce a desired pore shape and a desired pore size after the formation of pores.

In addition, the pore forming material according to the embodiment of the present disclosure has a wall portion formed of polyurethane or polyurea. Accordingly, in a case where the pore forming material is used such that the wall portion is removed by a heating treatment during the formation of pores, it is possible to suppress that the wall portion remains, and it is also possible to leave the pore forming material as it is in a molded product after molding.

Examples of the pore forming material include a pore forming material for porous ceramics for manufacturing porous ceramics, a pore forming material for a porous resin for manufacturing a porous resin, concrete for a building material, and concrete for civil engineering (for example, concrete for a road surface).

The pore forming material for porous ceramics can be used as, for example, a pore forming material for a ceramic filter or a ceramic artificial bone.

The pore forming material can be used as, for example, hollow microspheres described in JP2016-017026A or JP2009-527451A in order to impart freeze durability of concrete or to relax stress caused by freeze-thaw change.

Furthermore, the pore forming material can be used as, for example, hollow particles described in JP2015-137332A in order to improve the grip force of tires. Furthermore, the pore forming material can be used as, for example, hollow microelements described in JP2006-297497A to improve the polishing rate of a polishing sheet such as a silicon wafer. Furthermore, the pore forming material can be used as, for example, a foamed molded body described in JP2016-030394A in order to improve the impact absorption performance of an impact absorption film. Furthermore, the pore forming material can be used as, for example, hollow particles described in JP2010-275453A in order to improve the flexibility of an adhesive.

The pore forming material according to the embodiment of the present disclosure can also be used as a mixture with other raw materials. During mixing, for example, powdery hollow particles obtained by powderization and other desired raw materials are mixed. Examples of other raw materials include ceramic raw materials, various resins, adhesives, cement, mortar, and concrete.

<Particles for Cosmetics>

Particles for cosmetics according to the embodiment of the present disclosure include the hollow particles according to the embodiment of the present disclosure described above.

The particles for cosmetics according to the embodiment of the present disclosure have a wall portion formed of polyurethane or polyurea, and is thus thought to have oil absorbability or water absorbability derived from the properties of the polyurethane or polyurea and internal voids. Thus, the particles for cosmetics are suitable for use in cosmetics.

<Weight Reducing Material>

A weight reducing material according to the embodiment of the present disclosure includes the hollow particles according to the embodiment of the present disclosure described above.

The hollow particles according to the embodiment of the present disclosure have deformation resistance due to the internal porous structure thereof. Accordingly, in a case where the hollow particles are mixed into a desired material, breaking or destroying can be suppressed, and voids can be introduced in the material, whereby desired weight reduction can be realized. That is, since the hollow particles are hardly deformed in a case of being influenced by the properties of the material to be mixed, the mixing material, or the like, it is possible to reproduce a space with a desired shape and a desired size.

Furthermore, since the weight reducing material according to the embodiment of the present disclosure has a wall portion formed of polyurethane or polyurea as described above, it is possible to provide a weight reducing material in which a space having no wall portion is formed by finally performing a heating treatment for removing the wall portion. The weight reducing material may be used as described in the section of the pore forming material described above.

EXAMPLES

Hereinafter, the present invention will be described in greater detail with examples. However, the present invention is not limited to the following examples as long as the gist of the present invention is not impaired.

In these examples, preparation of microcapsules, which are an example of hollow particles, will be mainly described. However, hollow particles according to the embodiment of the present disclosure are not limited to the microcapsules shown in the examples.

In these examples, the volume-based median diameter was measured using Microtrac MT3300EXII (manufactured by Nikkiso Co., Ltd.). The thickness of a wall portion (wall thickness) was obtained by observing cross-sections of cut hollow particles with a scanning electron microscope JSM-7800F (manufactured by JEOL Ltd.) and by then measuring and averaging wall thicknesses (μm) of five hollow particles.

The boiling point was measured using a boiling point meter (DosaTherm 300, manufactured by Dosatec GmbH).

Tg was measured using a differential scanning calorimeter (DSC-60A, manufactured by Shimadzu Corporation).

The C Log P value was calculated using ChemBioDraw Ultra 13.0.

Example 1

50 parts by mass of ethyl butyrate (boiling point: 121° C.; a compound having a boiling point of 90° C. to 150° C.), 49.5 parts by mass of BURNOCK (registered trademark) D-750 (manufactured by DIC Corporation, tolylene diisocyanate-trimethylolpropane adduct; polyfunctional isocyanate compound), and 0.5 parts by mass of ADEKA POLYETHER EPD-300 (manufactured by ADEKA CORPORATION, N,N,N',N'-tetrakis(2-hydroxypropyl)ethylenediamine; polyether polyol) were mixed by stirring to obtain an oil phase.

Next, a 5 mass % aqueous solution of KURARAY POVAL (registered trademark) PVA-217E (manufactured by KURARAY CO., LTD., polyvinyl alcohol (PVA); emulsifier) was prepared. 100 parts by mass of the oil phase was added to 100 parts by mass of the aqueous solution, and the mixture was emulsified and dispersed at a rotation speed of 1,300 rpm (revolutions per minute) to prepare an emulsion (emulsion dispersion) (dispersion step). After the emulsification and dispersion, the prepared emulsion was heated to 70° C. to polymerize the aromatic polyisocyanate at the oil-water interface. Accordingly, a wall portion (shell) was formed, and an aqueous dispersion of microcapsules encapsulating the ethyl butyrate as a core component by the shell was obtained (particle forming step).

The volume-based median diameter (D50) of the microcapsules in the obtained aqueous dispersion was 15 μm.

Subsequently, the aqueous dispersion of microcapsules obtained as above was powderized by a spray dryer (Mini Spray Dryer B-290, manufactured by BUCHI Labortechnik AG), and further heat-treated in a dry oven at 150° C. for 3 hours to remove the ethyl butyrate from the inside of the microcapsules, and thus hollow microcapsules were formed (hollow particle forming step).

The volume-based median diameter (D50) of the hollow microcapsules, which are hollow particles, was 15 μm. The glass transition temperature (Tg) of the capsule wall (wall portion) of the hollow microcapsules was measured using a differential scanning calorimeter (DSC-60A, manufactured by Shimadzu Corporation), and the result was 105° C.

The particle shape (external shape) of the hollow microcapsules was confirmed by observing the surface of the hollow microcapsules with a scanning electron microscope JSM-7800F (manufactured by JEOL Ltd.).

The particle powder of the hollow microcapsules was attached to a PET film coated with a 5 mass % aqueous solution of PVA-217E (manufactured by KURARAY CO., LTD., polyvinyl alcohol (PVA)) as an adhesive. Then, a cut surface obtained by cutting with a microtome (EM UC7, manufactured by Leica Microsystems) was observed by a scanning electron microscope JSM-7800F (manufactured by JEOL Ltd.) to confirm the state (internal shape) in the particles of the hollow microcapsules.

The particles of the hollow microcapsules were cut, and the cut surface was observed by a scanning electron microscope JSM-7800F (manufactured by JEOL Ltd.). A ratio of the area of the hollow portion to the total area of the cut surface of the hollow particles was calculate, and thus a void volume (%) of the hollow microcapsules was calculated.

Examples 2 to 9

An aqueous dispersion of microcapsules was prepared in the same manner as in Example 1, except that the contents of the polyfunctional polyisocyanate, the polyol, and the organic solvent used for the preparation of the oil phase, or the rotation speed of stirring during emulsification was changed as shown in Table 1 in Example 1. After formation of hollow microcapsules, the particle shape and the state in the particles were confirmed, and the void volume was calculated.

Examples 10 to 11

An aqueous dispersion of microcapsules was prepared in the same manner as in Example 1, except that the kind of the organic solvent (the compound having a boiling point of 90° C. to 150° C.) or the rotation speed of stirring during emulsification was changed as shown in Table 1 in Example 1. After formation of hollow microcapsules, the particle shape and the state in the particles were confirmed, and the void volume was calculated.

Example 12

An aqueous dispersion of microcapsules was prepared in the same manner as in Example 1, except that a polyamine (tetraethylenepentamine, manufactured by Tosoh Corporation) was used instead of the polyol, and the glass transition temperature (Tg) of the capsule wall (wall portion) was changed as shown in Table 1 in Example 1. After formation of hollow microcapsules, the particle shape and the state in the particles were confirmed, and the void volume was calculated.

Example 13

An aqueous dispersion of microcapsules was prepared in the same manner as in Example 1, except that isobutyl acetate was used instead of the ethyl butyrate in Example 1. After formation of hollow microcapsules, the particle shape and the state in the particles were confirmed, and the void volume was calculated.

Example 14

An aqueous dispersion of microcapsules was prepared in the same manner as in Example 1, except that BURNOCK (registered trademark) D-750 as an aromatic polyisocyanate was changed to the same amount of TAKENATE (registered trademark) D-165N (manufactured by Mitsui Chemicals, Inc.) in Example 1. After formation of hollow microcapsules, the particle shape and the state in the particles were confirmed, and the void volume was calculated.

Comparative Examples 1 and 2

An aqueous dispersion of microcapsules was prepared in the same manner as in Example 1, except that the organic solvent (the compound having a boiling point of 90° C. to 150° C.) and the rotation speed of stirring during emulsification were changed as shown in Table 1 in Example 1. The aqueous dispersion was powderized, and heat-treated in a dry oven at 150° C. for 3 hours. Then, the particle shape and the state in the particles were confirmed, and the void volume was calculated in the same manner as in Example 1.

TABLE 1

| | Oil Phase | | | | | Water Phase | | Emulsification Conditions | Properties of Particles | | | | | |
|---|---|---|---|---|---|---|---|---|---|---|---|---|---|---|
| | Polyfunctional Polyisocyanate [parts by mass] | Polyol or Polyamine [parts by mass] | Compound Having Boiling Point of 90° C. to 150° C. or Comparative Compound | | | | | | Tg of Resin for Wall Portion | | | | |
| | | | Content (parts by mass) | Boiling Point [° C.] | ClogP | Dispersant [parts by mass] | Water [parts by mass] | Rotation Speed [rpm] | | External Shape | Internal Shape | Median Diameter (D50) | Void Volume |
| Example 1 | D-750 49.5 | Polyol 0.5 | Ethyl Butyrate 50 | 121 | 1.77 | PVA 5 | Water 95 | 1,300 | 105 | Spherical Shape | Porous Space | 15 μm | 48% |
| Example 2 | D-750 89.1 | Polyol 0.9 | Ethyl Butyrate 10 | 121 | 1.77 | PVA 5 | Water 95 | 1,800 | 105 | Spherical Shape | Porous Space | 15 μm | 11% |
| Example 3 | D-750 69.3 | Polyol 0.7 | Ethyl Butyrate 30 | 121 | 1.77 | PVA 5 | Water 95 | 1,500 | 105 | Spherical Shape | Porous Space | 15 μm | 29% |
| Example 4 | D-750 29.7 | Polyol 0.3 | Ethyl Butyrate 70 | 121 | 1.77 | PVA 5 | Water 95 | 1,100 | 105 | Spherical Shape | Porous Space | 15 μm | 66% |
| Example 5 | D-750 9.9 | Polyol 0.1 | Ethyl Butyrate 90 | 121 | 1.77 | PVA 5 | Water 95 | 1,000 | 105 | Spherical Shape | Porous Space | 15 μm | 82% |
| Example 6 | D-750 49.5 | Polyol 0.5 | Ethyl Butyrate 50 | 121 | 1.77 | PVA 5 | Water 95 | 12,000 | 105 | Spherical Shape | Porous Space | 0.1 μm | 40% |
| Example 7 | D-750 49.5 | Polyol 0.5 | Ethyl Butyrate 50 | 121 | 1.77 | PVA 5 | Water 95 | 7,000 | 105 | Spherical Shape | Porous Space | 1 μm | 45% |
| Example 8 | D-750 49.5 | Polyol 0.5 | Ethyl Butyrate 50 | 121 | 1.77 | PVA 5 | Water 95 | 700 | 105 | Spherical Shape | Porous Space | 50 μm | 48% |
| Example 9 | D-750 49.5 | Polyol 0.5 | Ethyl Butyrate 50 | 121 | 1.77 | PVA 5 | Water 95 | 350 | 105 | Spherical Shape | Porous Space | 500 μm | 51% |
| Example 10 | D-750 49.5 | Polyol 0.5 | Amyl Acetate 50 | 149 | 1.62 | PVA 5 | Water 95 | 1,200 | 105 | Spherical Shape | Porous Space | 15 μm | 49% |
| Example 11 | D-750 49.5 | Polyol 0.5 | γ-Nonalactone 50 | 136 | 1.83 | PVA 5 | Water 95 | 1,300 | 105 | Spherical Shape | Porous Space | 15 μm | 46% |
| Example 12 | D-750 49.5 | Polyol 0.5 | Ethyl Butyrate 50 | 121 | 1.77 | PVA 5 | Water 95 | 1,300 | 110 | Spherical Shape | Porous Space | 15 μm | 49% |
| Example 13 | D-750 49.5 | Polyol 0.5 | Isobutyl Acetate 50 | 118 | 1.64 | PVA 5 | Water 95 | 1,300 | 105 | Spherical Shape | Porous Space | 15 μm | 48% |
| Example 14 | D-165N 49.5 | Polyol 0.5 | Ethyl Butyrate 50 | 121 | 1.77 | PVA 5 | Water 95 | 1,300 | 90 | Spherical Shape | Porous Space | 15 μm | 49% |
| Comparative Example 1 | D-750 49.5 | Polyol 0.5 | Ethyl Acetate 50 | 77 | 0.71 | PVA 5 | Water 95 | 1,200 | 105 | Spherical Shape | Porous Space | 15 μm | 0% |
| Comparative Example 2 | D-750 49.5 | Polyol 0.5 | Decane 50 | 174 | 5.98 | PVA 5 | Water 95 | 1,200 | 105 | Spherical Shape | Porous Space | 15 μm | 48% |

As shown in Table 1, in the examples, it was possible to obtain hollow particles having an internal porous structure, and the hollow particles had elasticity and excellent deformation resistance. In the obtained hollow particles, a plurality of opening spaces existing in an outermost portion of the porous structure were blocked by the capsule wall (wall portion).

In contrast, in Comparative Example 1 in which an organic solvent having a boiling point of lower than 90° C. was used instead of the "compound having a boiling point of 90° C. to 150° C." used in the examples, it was not possible to form hollow particles. On the contrary, in Comparative Example 2 in which an organic solvent having a boiling point of higher than 150° C. was used instead of the "compound having a boiling point of 90° C. to 150° C." used in the examples, hollow particles were obtained, but it was not possible to form particles having an internal porous structure.

Hollow particles and a manufacturing method thereof according to the embodiment of the present disclosure can be suitably used in any field using the hollow particles.

Specifically, the hollow particles are suitably used for a material requiring various functions such as a heat insulation property, elasticity, a soundproofing property, and vibration resistance by using the heat insulation function, elasticity, soundproofing function, and the like thereof. In addition, the hollow particles according to the embodiment of the present disclosure are suitably used in a material for forming a space (for example, a pore forming material or a weight reducing material) since the wall portion thereof is an organic material containing polyurethane or polyurea. The hollow particles according to the embodiment of the present disclosure are also suitable for cosmetics and the like.

The disclosures of JP2018-056909 filed on Mar. 23, 2018, and JP2018-202215 filed on Oct. 26, 2018 are incorporated herein by reference in their entirety.

All literatures, patent applications, and technical standards described herein are incorporated herein by reference to the same extent as if each literature, patent application, or technical standard is specifically and individually indicated as being incorporated by reference.

What is claimed is:

1. Hollow particles which have a wall portion containing polyurethane or polyurea, have an internal porous structure, and have a plurality of opening spaces blocked by the wall portion in an outermost portion of the porous structure, wherein the particles have a volume-based median diameter greater than or equal to 15 μm and less than 200 μm.

2. The hollow particles according to claim 1, wherein the particles have a void volume of 10% to 90%.

3. The hollow particles according to claim 1, wherein the particles have a spherical particle shape.

4. A pore forming material comprising: the hollow particles according to claim 1.

5. The pore forming material according to claim 4, wherein the material is used for manufacturing porous ceramics or a porous resin.

6. Particles for cosmetics which have oil absorbability or water absorbability, comprising: the hollow particles according to claim 1.

7. A weight reducing material comprising: the hollow particles according to claim 1.

8. A hollow particle manufacturing method comprising:
dispersing an oil phase containing a polyfunctional isocyanate compound, a compound having a boiling point of 90° C. to 150° C., and at least one of a polyol or a polyamine in a water phase to prepare a dispersion liquid;
heat-treating the dispersion liquid to polymerize at least the polyfunctional isocyanate compound, thereby forming a wall portion, and obtaining particles encapsulating the compound having a boiling point of 90° C. to 150° C.; and
removing the compound having a boiling point of 90° C. to 150° C. from the particles by a heating treatment to form hollow particles having a porous structure, wherein the particles have a volume-based median diameter greater than or equal to 15 and less than 200 μm.

9. The hollow particle manufacturing method according to claim 8,
wherein a glass transition temperature of a resin as a wall material for the wall portion of the particles is equal to or lower than the boiling point of the compound having a boiling point of 90° C. to 150° C.

10. The hollow particle manufacturing method according to claim 8,
wherein a C log P value of the compound having a boiling point of 90° C. to 150° C., which is a partition coefficient, is 1 to 4.

11. Hollow particles manufactured by the hollow particle manufacturing method according to claim 8.

12. Hollow particles manufactured by the hollow particle manufacturing method according to claim 9.

13. Hollow particles manufactured by the hollow particle manufacturing method according to claim 10.

14. The hollow particles according to claim 1,
wherein the polyurethane and the polyurea have a structure derived from aliphatic polyisocyanate.

15. The hollow particle manufacturing method according to claim 8,
wherein the polyfunctional isocyanate compound comprises aliphatic polyisocyanate.

* * * * *